(12) United States Patent
Czarniecki (10) Patent No.: US 11,172,694 B2
(45) Date of Patent: Nov. 16, 2021

(54) CORE-SHELL STRUCTURE WITH TITANIUM DIOXIDE CORE

(71) Applicant: SOLID CHEMICALS GMBH, Gossau (CH)

(72) Inventor: Janusz Czarniecki, Gossau (CH)

(73) Assignee: SOLID CHEMICALS GMBH, Gossau (CH)

( * ) Notice: Subject to any disclaimer, the term of this patent is extended or adjusted under 35 U.S.C. 154(b) by 0 days.

(21) Appl. No.: 16/328,113

(22) PCT Filed: Aug. 22, 2017

(86) PCT No.: PCT/EP2017/071158
§ 371 (c)(1),
(2) Date: Feb. 25, 2019

(87) PCT Pub. No.: WO2018/037018
PCT Pub. Date: Mar. 1, 2018

(65) Prior Publication Data
US 2019/0183146 A1    Jun. 20, 2019

(30) Foreign Application Priority Data
Aug. 25, 2016   (EP) .................... 16185617

(51) Int. Cl.
*A23K 40/30* (2016.01)
*A23K 20/20* (2016.01)
(Continued)

(52) U.S. Cl.
CPC .............. *A23K 40/30* (2016.05); *A23K 20/20* (2016.05); *A23K 20/30* (2016.05); *A23K 50/30* (2016.05);
(Continued)

(58) Field of Classification Search
CPC ........ A23K 50/60; A23K 40/30; A23K 20/30; A23K 50/30; A23K 20/20; A61K 33/00; A61K 9/5015; A61P 1/12
See application file for complete search history.

(56) References Cited

U.S. PATENT DOCUMENTS

2003/0148013 A1   8/2003  Jobe et al.
2004/0009349 A1   1/2004  Brotzman, Jr. et al.
(Continued)

FOREIGN PATENT DOCUMENTS

EP        0 401 045 A1   12/1990
KR        2011-0012795 A   2/2011

OTHER PUBLICATIONS

Stein, ("Feeding the Pigs' Immune System and Alternatives To Antibiotics," in Proceedings London Swine Conference—Today's Challenges, Tomorrow's Opportunity, 2007, pp. 65-82.*
(Continued)

*Primary Examiner* — Blessing M Fubara
(74) *Attorney, Agent, or Firm* — Finch & Maloney, PLLC; Michael J. Bujold; Jay S. Franklin (57) ABSTRACT

A core-shell structure (1) comprising a core (2) of titanium oxide and a shell (3) essentially comprising, preferably consisting, of an oxide of an element selected from a group consisting of zinc, copper, vanadium, chromium, manganese, cobalt, molybdenum, tungsten, silver and mixtures thereof. A method for making a core-shell structure, in particular a core-shell structure (1) as described above, and the use of a plurality of such core-shell structures (1) as a food additive, a feed additive, in a feed stuff or as a medicament.

14 Claims, 6 Drawing Sheets

(51) Int. Cl.
   A23K 50/30    (2016.01)
   A23K 50/60    (2016.01)
   A61K 9/50     (2006.01)
   A61K 33/00    (2006.01)
   A61K 33/30    (2006.01)

(52) U.S. Cl.
   CPC ............ *A23K 50/60* (2016.05); *A61K 9/5015* (2013.01); *A61K 33/00* (2013.01); *A61K 33/30* (2013.01)

(56) References Cited

U.S. PATENT DOCUMENTS

| | | |
|---|---|---|
| 2005/0182152 A1 | 8/2005 | Nonninger et al. |
| 2007/0280895 A1* | 12/2007 | Weimer et al. ......... A61K 8/29 424/459 |
| 2008/0061068 A1 | 3/2008 | Fontaine et al. |
| 2010/0310774 A1* | 12/2010 | Wu .................... C09D 7/62 427/331 |

OTHER PUBLICATIONS

Annon, "Zincoat," Jun. 24, 2011, http:J/www.orffa.com/products/e:x.cential-zincoat.*

Selvi et al, ("Effect of shell ZnO on the structure and optical property of TiO2 core@shell hybrid nanoparticles," in J. Mater. Sci. Materials in Electronics, vol. 26, No. 4, Jan. 13, 2015, 2271-2277).*

Waititu et al. (Dose-response effects of in-feed antibiotics on growth performance and nutrient utilization in weaned pigs fed diets supplemented with yeast-based nucleotides in Animal Nutrition 1, (2015) 166-169).*

Computer Translation of JP 2004177747, 2004, Description.*

Computer Translation of JP 2004177747, 2004, Claims.*

2010 EPA Nano material Case studies: Nano scale titanium dioxide.*

Yang et al., Food Grade Titanium Dioxde: The presence of nanosized particles, Environmetal Science Technology, Apr. 2014.*

Stein et al., "Feeding the Pigs' Immune System and Alternatives to Antibiotics", Proceedings London Swine Conference—Today's Challenges—Tomorrow's Opportunities, 2007, pp. 65-82.

Myachoti et al., "Feed Additives and Feeding Strategies to Replace Antibiotics", Advances in Pork Production, 2013, 24, pp. 123-127.

Selvi et al., "Effect of Shell ZnO on the Structure and Optical Property of TiO2 core@shell Hybrid Nanoparticles", Journal of Materials Science Materials in Electronics, vol. 26, No. 4, Jan. 13, 2015, pp. 2271-2277.

Anon , "Zincoat", Jun. 24, 2011, http://www.orffa.com/products/excential-zincoat.

Kwon et al., "Effects of Dietary Supplementation of Lipid-Encapsulated Zinc Oxide on Colibacillosis, Growth and Intestinal Morphology in Weaned Piglets Challeneged with Enterotoxigenic *Escherichia coli*", Animal Science Journal, vol. 85, No. 8, Aug. 1, 2014.

Gill et al., "Alternatives to Antibiotic Feed Additives for Pigs", BSAS, Jul. 1, 2005, 4 pages.

Shourong Shi, "Alternatives to Antibiotics as Growth Promoters For Use in Animal Production", Poultry Institute, Chinese Academy of Agricultural Sciences, Mar. 11, 2015, 38 pages.

Philip A. Thacker, "Alternatives to Antibiotics as Growth Promoters for use in Swine Production: A Review", Journal of Animal Science and Biotechnology, 2013, pp. 1-12.

Trackova et al., "Prophylaxis of Post-Weaning Diarrhoea in Piglets by Zinc Oxide and Sodium Humate", Veterinarni Medicina, vol. 60, No. 7, 2015, pp. 351-360.

International Search Report Corresponding to PCT/EP2017/071158 dated Oct. 20, 2017.

Written Opinion Corresponding to PCT/EP2017/071158 dated Oct. 20, 2017.

* cited by examiner

CORE-SHELL STRUCTURE WITH TITANIUM DIOXIDE CORE

The present invention refers to a core-shell structure, a method for making a core-shell structure and the use of a plurality of core-shell structures according to the independent claims.

Piglets are highly susceptible to enteric disorders immediately after weaning. They then have an immature digestive system, the capacity of which for nutrient digestion is impaired by the transition from sow milk to a solid diet. Diarrhea is a common post-weaning disease that is characterized by reduced digestive capacity leading to poor growth performance. Because of the immature microflora, proliferation of enteropathogenic bacteria has a high incidence that further predisposes piglets to enteric infections.

In order to mitigate these effects, weaned piglets were fed in the past with diets routinely supplemented with subtherapeutic levels of antibiotics as growth promoters (AGPs). However, AGPs are suspect of increasing the antibiotics resistance of pathogenic bacteria, which is a potential risk to human health. AGPs have therefore been banned from swine production in many countries and are under pressure to be banned globally.

These developments have sparked considerable interest in identifying alternative nutritional strategies in pig feeding. Various different approaches have been developed relying on novel feed additives or alternative feeding strategies. An overview of the progress in this field has been provided in two review articles (H. H. Stein, Feeding the Pigs' Immune System and Alternatives to Antibiotics, Proceedings London Swine Conference—*Today's Challenges—Tomorrow's Opportunities* 2007, 65-82; M. Nyachoti, J. M. Heo, Feed Additives and Feeding Strategies to Replace Antibiotics, *Advances in Pork Production* 2013, 24, 123-127).

A widely employed alternative to AGPs is the supplementation of the pig's diet with pharmacological levels (3000-4000 ppm) of zinc oxide (ZnO). Zinc oxide shows similar effects on daily growth and feed conversion rates as antibiotics employed as growth promoters. Thus, zinc oxide fed at pharmacological levels can be a cost-effective strategy for controlling post weaning diarrhea. The approach does not affect the resistance of bacteria. However, with such high levels of zinc oxide, concerns about adverse environmental effects (accumulation of heavy metal salts in the environment) have arisen. This has led to a restrictive use of this method. According to regulation No. 1831/2003 by the European Commission, 150 ppm of zinc is allowed in compound feedstuff in the European Union. Switzerland knows the same maximum value for young farmed animals (cf. Liste der zugelassenen Futtermittelzusatzstoffe (Zusatzstoffliste 2)).

Orffa Additives B.V. (NL) distributes micro-encapsulated zinc oxide for the prevention of post-weaning diarrhea in piglets. It is surmised that, when passing the piglet's stomach, zinc oxide is partially converted into zinc chloride which does not show the desired properties. By micro-encapsulation with a vegetable fatty acid matrix, zinc oxide is prevented from these reactions. When entering the intestines, the coating is digested by lipase and bile salts, and zinc oxide is released. Due to its increased efficacy, micro-encapsulated zinc oxide can be used at levels a ten-fold lower than common inorganic zinc oxide, maintaining similar results on diarrhea prevention and production performance. However this is still not sufficient to meet the new regulations.

It is therefore a problem underlying the present invention to overcome the above-mentioned drawbacks in the prior art. In particular, it is a problem underlying the present invention to provide a feed additive or feedstuff, which shows similar or even better growth and feed conversion rates than those achieved with subtherapeutic antibiotics or pharmacological levels of zinc oxide in the feeding of weaned piglets. More particularly, the heavy metal concentrations that are to be achieved in a compound feedstuff are less than 100 ppm. This is in line with current regulatory allowances.

This problem is solved by a core-shell structure, a method for making a core-shell structure and the use of a plurality of core-shell structures in a feed additive or feed stuff comprising the features in the independent claims.

The core-shell structure comprises a core of titanium oxide and a shell essentially comprising, preferably consisting of, an oxide of an element selected from a group consisting of zinc, copper, vanadium, chromium, manganese, cobalt, molybdenum, tungsten, silver and mixtures thereof.

By providing these heavy metal oxides in the form of a core-shell structure, their concentration in a feed additive or feed stuff can be significantly reduced without diminishing their activity. Similar growth and feed conversion rates as those achieved with high dosages of zinc oxide reported in the literature can be achieved at substantially lower heavy metal loadings.

The core-shell structure can have a specific surface of at least 20 $m^2/g$, preferably at least 60 $m^2/g$, more preferably at least 120 $m^2/g$. In certain embodiments, the core-shell structure can have a specific surface between 20 $m^2/g$ and 200 $m^2/g$, in particular between 40 $m^2/g$ and 160 $m^2/g$ or between 60 $m^2/g$ and 120 $m^2/g$. Such high specific surfaces can be achieved with porous shells. This allows for a further increase of the active surface of the heavy metal oxides and therefore for even better growth and feed conversion rates at lower dosages.

In the context of the present invention, specific surfaces are determined with the BET-method, specifically according to the norm DIN-ISO 9277.

In the context of the present invention, the core shell-structure further comprises a hydrophobic coating, preferably on top of the shell, in particular of at least one lipid. It has been found that core-shell structures of the above-mentioned kind exhibit a significantly better growth and feed conversion rate, if they bear a hydrophobic coating. Therefore the heavy metal loadings can be further reduced and the results achieved are superior to those attained with subtherapeutic antibiotics or pharmacological levels of zinc oxide. The heavy metal concentrations can be reduced to less than 100 ppm in a compound feed, which is well in-line with current regulatory allowances.

However, there is also disclosed a core-shell structure as described hereinabove, which comprises no hydrophobic coating.

The at least one lipid can be a fatty acid, in particular an unsaturated or a saturated fatty acid. Fatty acids show high biocompatibility and, hence, a better growth and feed conversion rates. The fact that either unsaturated or saturated fatty acids can be used allows for adapting the kind of fatty acid employed to other constituents of a compound feedstuff. The fatty acids can be selected from a group consisting of myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid and erotic acid.

In a plurality of core-shell structures of the above-mentioned kind, the diameter of 90% of the cores can be in a range between 0.01 µm and 100 µm, preferably between 0.1 µm and 10 µm, more preferably between 0.15 µm and 0.75 µm. With this particle size distribution, optimal results are achieved.

Disclosed is also a method for making a core-shell structure. The method comprises the steps of:
Providing a core of titanium oxide;
Treating the core with an ammonium salt and a metal salt, in particular a salt of a metal selected from a group consisting of zinc, copper, vanadium, chromium, manganese, cobalt, molybdenum, tungsten, silver and mixtures thereof, to obtain an intermediate;
Calcining the intermediate to obtain a core-shell structure;
Optionally: Coating the core-shell structure obtained with a hydrophobic coating, preferably on top of the shell, in particular of at least one lipid, to obtain a coated core-shell structure.

The described method allows for efficient production of various core-shell structures. Furthermore, the method is highly versatile, as a large range of different structures can be produced by employing different combinations of starting materials.

The present invention further refers to a method for making a core-shell structure as described above. The method comprises the steps of:
Providing a core of titanium oxide;
Treating the core with an ammonium salt selected from a group consisting of ammonium carbamate and ammonium carbonate and with a metal salt, in particular a salt of a metal selected from a group consisting of zinc, copper, vanadium, chromium, manganese, cobalt, molybdenum, tungsten, silver and mixtures thereof, to obtain an intermediate;
Calcining the intermediate to obtain a core-shell structure;
Coating the core-shell structure obtained with a hydrophobic coating, preferably on top of the shell, in particular of at least one lipid, to obtain a coated core-shell structure.

The above-mentioned ammonium salts lead to intermediates that are particularly susceptible to calcination. The metal salt used can be a halide, preferably a chloride. These are abundantly available at low prices.

In such a method, a plurality of cores of titanium oxide can be provided and the diameter of 90% of the cores can be in a range between 0.01 µm and 100 µm, preferably between 0.1 µm and 10 µm, more preferably between 0.15 µm and 0.75 µm.

In the above-described methods, the step of treating the core with an ammonium salt and a metal salt can be conducted in presence of a template. Such a template leads to an increased surface area of the shell. Preferably, the template can be a fat suspension.

The present invention further refers to a food additive, a feed additive or a feed stuff comprising a plurality of core-shell structures as described above.

Such a food additive, feed additive or feedstuff can comprise core-shell structures with copper and zinc, either separate or in combination, wherein the ratio between copper and zinc is in a range between 1:100 and 1:1, preferably between 1:50 and 1:2, most preferably between 1:20 and 1:5. With such a combination, good results can be achieved with respect to growth and feed conversion rates at particularly low heavy metal loadings.

The present invention further refers to the non-therapeutic use of a plurality of core-shell structures of the above-described kind as a food additive, feed additive or in a feedstuff. However, it has to be noted that the use of such core-shell structures is by no means restricted to such applications. By way of example, core-shell structures of the above mentioned kind may also be employed in cosmetics.

Furthermore, a plurality of core-shell structures according to the present invention can also be for use as a medicament, in particular for use in the treatment of diarrhea or food poisoning.

Further advantages and features of the present invention become apparent from the following discussion of several embodiments and from the figures. It is shown in
FIG. 1: Schematic representation of a core-shell structure according to the present invention.

A variety of core-shell structures were prepared and tested in vivo. For illustration, the preparation of a structure with a shell of ZnO and a coating of fatty acids having an overall zinc content of 10% is discussed in the following:

$TiO_2$ (5 kg) was added to water (20l). The resulting mixture was stirred vigorously until it became homogenous. Ammonium carbamate (630 g) was added and stirring was repeated until the mixture was homogenous again. A solution of $ZnCl_2$ (4325 g) in water was added and vigorous stirring was continued, during which gas-evolution and the formation of a foam-like gel was observed. After gas-evolution had ceased, the gel was allowed to stand for several hours. The mixture was filtered and the resulting residue was washed with water (three times). The solid obtained was dried at 120° C. until its weight was constant and then subjected to calcination at 400° C. The calcinated material was sieved and coated with a mixture of fatty acids ($C_{12}$ to $C_{20}$ saturated and unsaturated fatty acids) by spraying the material with the mixture.

Upon addition of $ZnCl_2$ to the mixture, the following reaction occurs:

$$5ZnCl_2 + 5NH_2CO_2NH_4 + 8H_2O \rightarrow Zn_5(OH)_6(CO_3)_2(s) + 3CO_2(g) + 10NH_4Cl$$

Due to the $CO_2$ gas generated, the $Zn_5(OH)_6(CO_3)_2$ forms as a foam-like gel that settles on the titanium oxide. After filtration and drying, the coated $TiO_2$ is subjected to calcination in order to obtain a highly porous coating of zinc oxide:

$$Zn_5(OH)_6(CO_3)_2(s) \rightarrow 5ZnO(s) + 2CO_2(g) + 3H_2O$$

The core-shell structures obtained can optionally be coated with a hydrophobic material, in particular with a lipid, such as a fatty acid. By employing this method, various materials according to the present invention were prepared with different heavy metals, contents thereof and coatings.

In the above procedure, a template was optionally added in order to increase to surface area of the zinc oxide. The template was prepared by mixing sunflower oil (100 g), Tween 20 (10 g) and octanol (10 ml) in a blender. The resulting mixture was added to the $TiO_2$ slurry together with the ammonium carbamate. The $Zn_5(OH)_6(CO_2)_2$ was thus formed in presence of the template. During calcination, the template was degraded to afford the zinc oxide in highly porous form.

Figure 1:
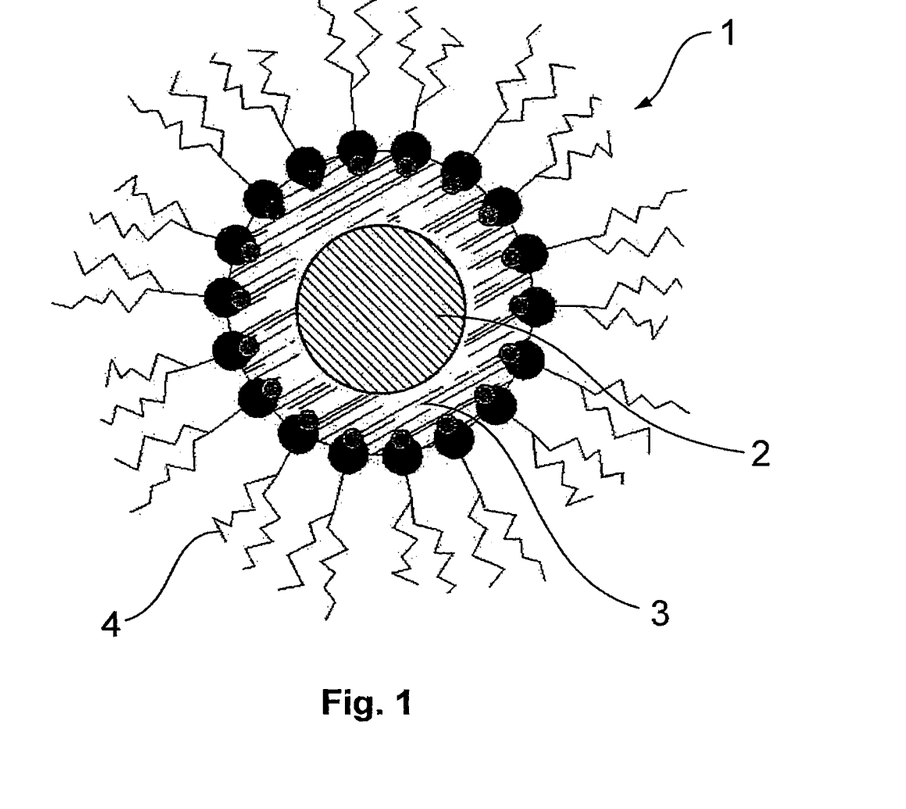

FIG. 1 provides a schematic representation of the core-shell structure 1 prepared in the above-mentioned example. The core 2 of $TiO_2$ is coated with a shell 3 of porous ZnO.

Furthermore, the whole particle is coated with a layer 4 of fatty acids. The carboxylic acid residues of the fatty acids are presumed to adhere on the surface of ZnO, rendering the exterior of the core-shell structure hydrophobic. It is reasonable to assume that this hydrophobic coating protects the structure, in particular the layer of ZnO, against gastric acid when passing the pig's gastric-intestinal tract. The coating is then presumably degraded in the intestine, setting free the uncoated particle.

Table 1 provides an overview of the materials subjected to in vivo testing:

TABLE 1

Overview of materials subjected to in vivo testing

| Run | Material Tested | Composition of Core-Shell Structure | Coating | Health Condition of Animals | Results in FIG. |
|---|---|---|---|---|---|
| 1 | L-Zn (50 ppm) | TiO$_2$/ZnO (10% Zn) | none | fair | 2/3 |
|   | H—Zn (100 ppm) | TiO$_2$/ZnO (20% Zn) | none |  |  |
| 2 | Zn 50 ppm (P) | TiO$_2$/ZnO (10% Zn) | paraffin oil | good | 4/5 |
|   | Zn 50 ppm (S) | TiO$_2$/ZnO (10% Zn) | sunflower oil |  |  |
| 3 | Zn 50 ppm (S) | TiO$_2$/ZnO (10% Zn) | sunflower oil | fair | 6/7 |
|   | Zn 50 ppm (FA) | TiO$_2$/ZnO (10% Zn) | fatty acids |  |  |
| 4 | Zn 50 ppm (FA) | TiO$_2$/ZnO (10% Zn) | fatty acids | fair | 8/9 |
|   | Zn/Cu (FA) 50 ppm | 95% TiO$_2$/ZnO (10% Zn) 5% TiO$_2$/CuO (10% Cu) | fatty acids |  |  |
| 5 | Zn 50 ppm (FA) | TiO$_2$/ZnO (10% Zn) | fatty acids | poor | 10/11 |
|   | Zn/Cu (FA) 50 ppm | 95% TiO$_2$/ZnO (10% Zn) 5% TiO$_2$/CuO (10% Cu) | fatty acids |  |  |

In these experiments, the core-shell structures were used as a feed additive for weaned piglets. Each run was conducted with two groups of about 50 animals, which were fed with two different feedstuff compositions. The results obtained were compared to those of a control group ("Null"), which obtained the same diet, but without additive. The weight of the animals was recorded at regular intervals. The results shown in the figures reflect the weight after approximately one month of feeding. The dosage of feed additive was always 500 g per ton feedstuff. This generally corresponds to an overall heavy metal content of 50 ppm.

Figure 2:
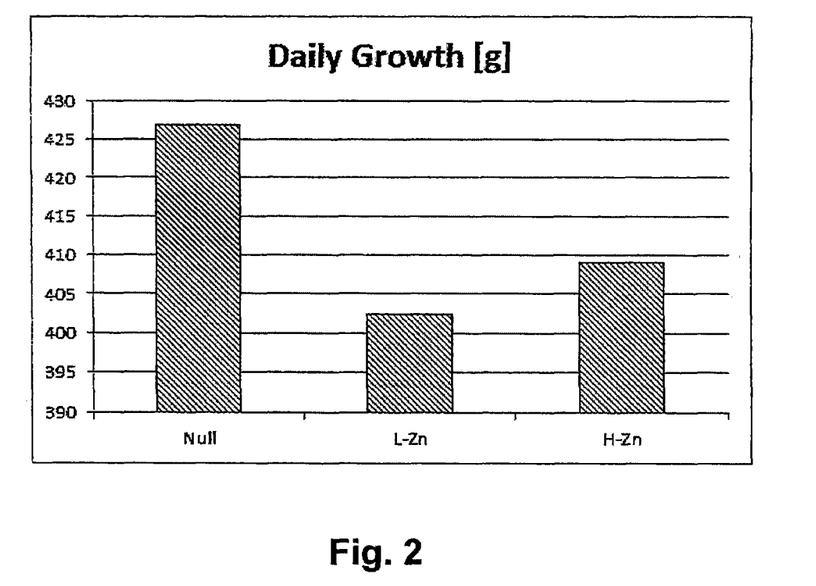
FIGS. 2 to 11: Experimental results of in vivo studies conducted with several core-shell structures.
Figure 3:
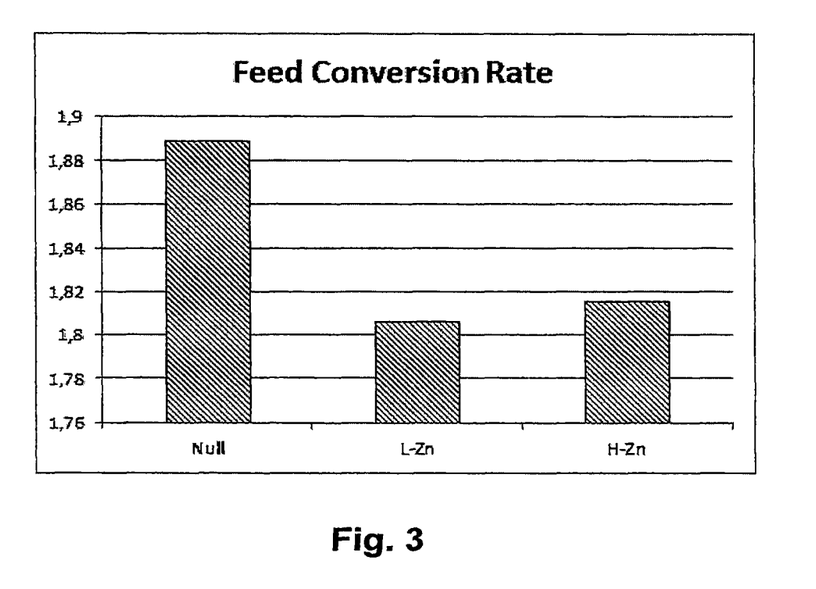

FIGS. 2 and 3 summarize the results of the first experiment, in which two uncoated core-shell structures were tested. The first structure (L-Zn) was based on a core of TiO$_2$ with a coating of ZnO. The material had a zinc content of 10%. The second material tested (H—Zn) had the same structure, but had a zinc content of 20%.

The health condition of the animals was fair, which can be considered as normal for piglets after weaning. As can be seen from FIG. 2, both feed additives led to a slightly diminished daily growth rate (the higher, the better) compared to the control group. However, the results in FIG. 3 clearly show that an improved feed conversion rate (the lower, the better) was achieved. Surprisingly, the material having the lower zinc content (L-Zn) showed a more pronounced effect than the material with the higher zinc content (H—Zn).

Figure 4:
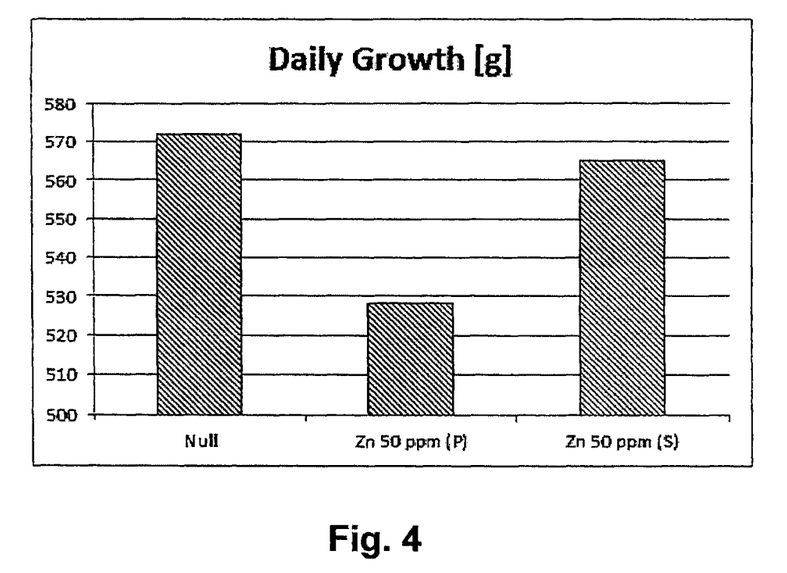
Figure 5:
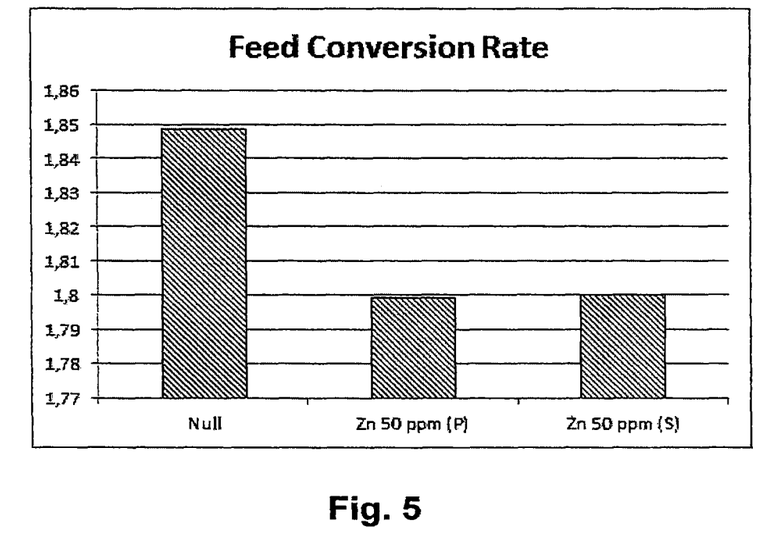

FIGS. 4 and 5 show the results of Experiment 2. Here, the core-shell structures with the low zinc content of 10% (L-Zn) were coated with two different oils, namely paraffin oil (P) and sunflower oil (S). The overall amount of zinc in the supplemented feedstuff was 50 ppm in both cases. The health condition of the piglets fed was comparably good. It becomes apparent from FIG. 4 that both materials tested still led to a lower daily growth rate than observed with the control group. However, the material coated with sunflower oil only showed a slightly negative effect. On the other hand, as can be seen in FIG. 5, a significantly improved feed conversion rate was observed with both materials.

Figure 6:
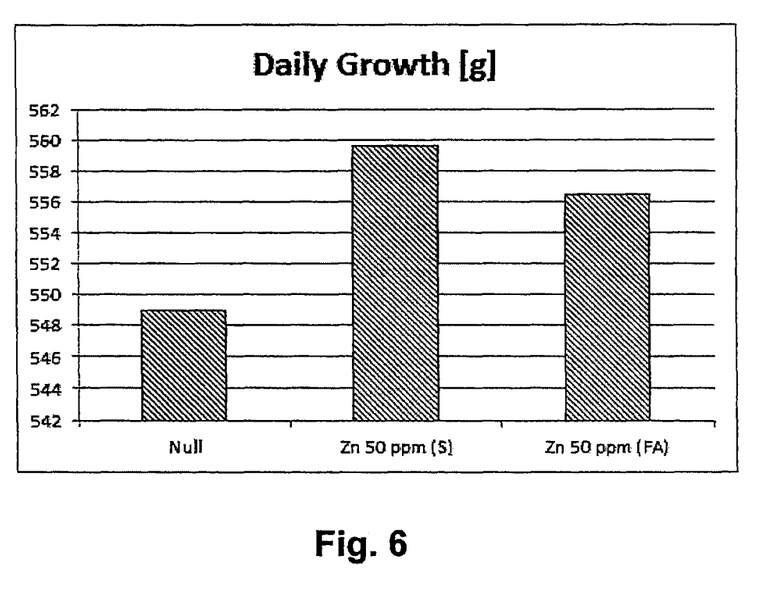
Figure 7:
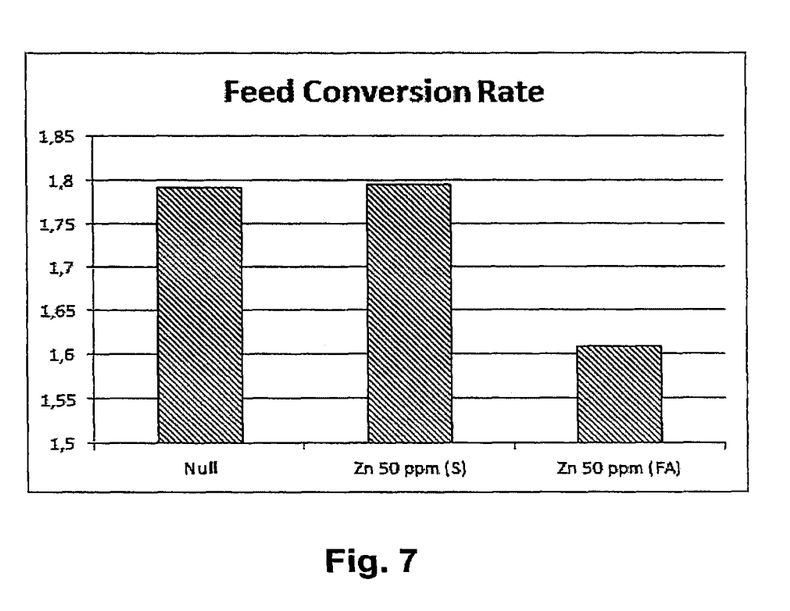

FIGS. 6 and 7 summarize the results of Experiment 3. Here, the core-shell structures coated with sunflower oil (S) were compared to an analogous material with a fatty acid coating (FA). The overall health condition of the animals was only fair. Presumably, this is the reason as to why an improved daily growth rate compared to the control group was observed this time with both samples, which becomes apparent from FIG. 6. FIG. 7 reveals that, in this case, the structures coated with sunflower oil led to a feed conversion rate comparable to that of the control group. Surprisingly, a significant improvement of the feed conversion rate was observed for the core-shell structures coated with fatty acids.

Figure 8:
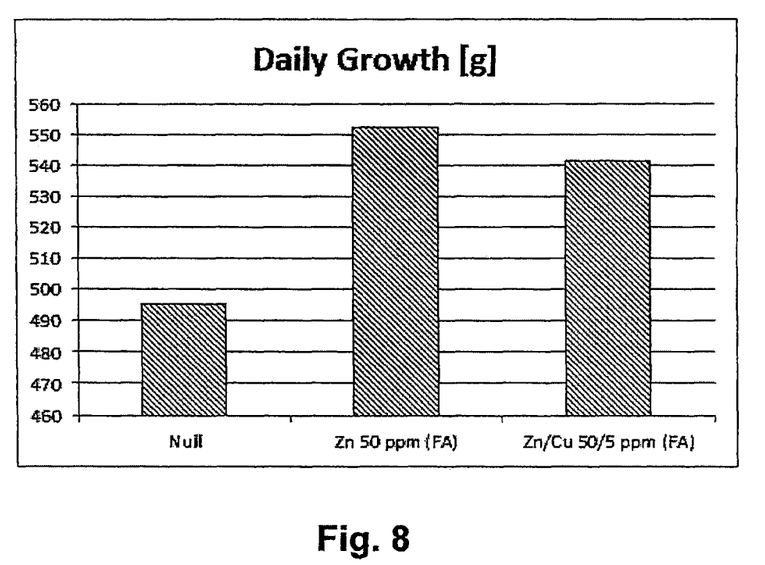
Figure 9:
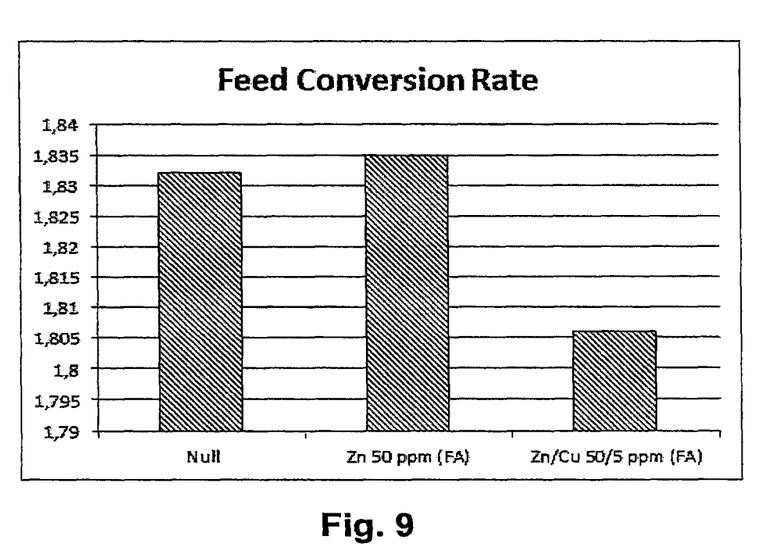

FIGS. 8 and 9 summarize the results of Experiment 4. Here, the core-shell structures of Experiment 3 coated with fatty acids were compared to a feed additive consisting of fatty acid-coated core-shell structures based on ZnO or CuO, respectively. The content of zinc and copper was 10% in both kinds of material. In the feedstuff formulation, 95% of zinc-based structures were used with 5% of copper-based ones. This again corresponds to an overall heavy metal content of 50 ppm in the feedstuff.

The health condition of the animals was fair. As apparent from FIG. 8, an increase of the daily growth rate could be achieved with both materials. FIG. 9 reveals that a slightly inferior feed conversion rate was observed with the material that was exclusively based on zinc oxide. In contrast, the combination of zinc and copper led to a significant improvement of the feed conversion rate. Indeed, the feed additive based on the oxides of copper and zinc led to results, which were clearly superior to those normally observed with pharmalogical levels (3000 to 4000 ppm) of conventional zinc oxide.

Figure 10:
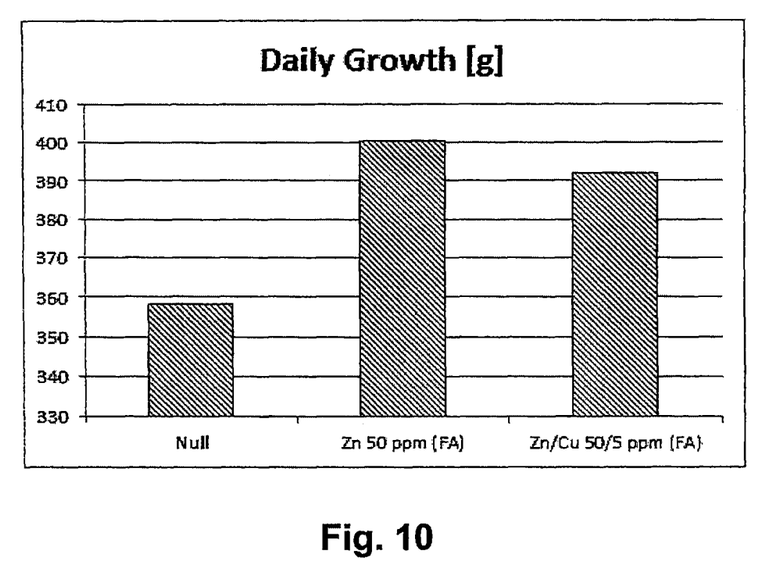
Figure 11:
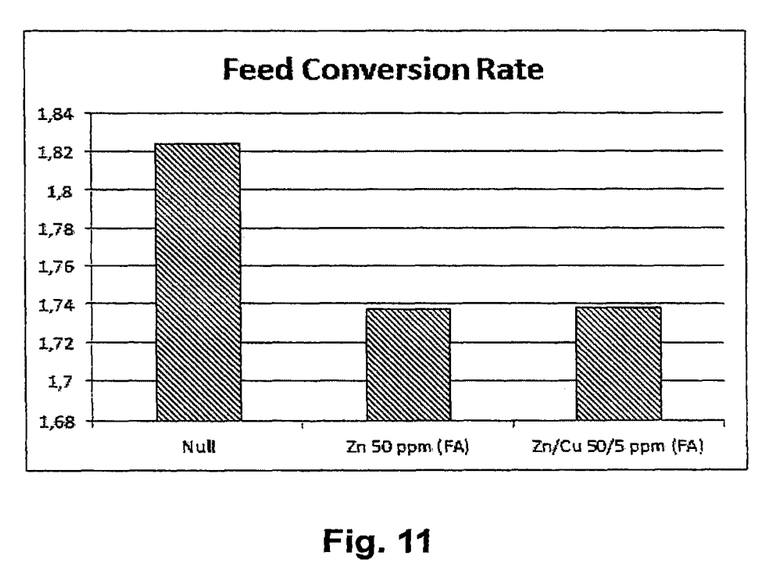

FIGS. 10 and 11 show the results of Experiment 5. The same materials as in the previous one were tested here, but the overall health condition of the animals was poor this time. FIG. 10 indicates that both feed additives led to an increase of the daily growth rate. As shown in FIG. 11, no significant difference in the feed conversion rate between the materials was observed this time. Apparently, the beneficial effect of copper on the feed conversion rate only has an influence, if the health condition of the animals is compromised.

In conclusion, a feed additive is provided, which leads to similar or even better growth and feed conversion rates than those achieved with subtherapeutic antibiotics or pharmacological levels of zinc oxide. Most notably, the heavy metal concentrations in compound feedstuffs are well below 100 ppm.

The invention claimed is:

1. A plurality of core-shell structures, wherein the core-shell structure comprising a core of titanium oxide and a shell essentially comprising an oxide of a heavy metal selected from a group consisting of zinc, copper, vanadium, chromium, manganese, cobalt, molybdenum, tungsten, silver and mixtures thereof,
   wherein the core-shell structure has a specific surface of at least 20 m$^2$/g, and comprises a hydrophobic coating of at least one lipid, and
   wherein a concentration of the heavy metal of the core-shell structures is less than 100 ppm, and a diameter of 90% of the cores of the core-shell structures is in a range between 0.01 μm and 100 μm.

2. The plurality of core-shell structures according to claim 1, wherein the specific surface of the core-shell structure is at least 60 m$^2$/g.

3. The plurality of core-shell structures according to claim 2, wherein the specific surface of the core-shell structure is at least 120 m$^2$/g.

4. The plurality of core-shell structures according to claim 1, wherein the at least one lipid is a fatty acid, and the fatty acid is either an unsaturated fatty acid or a saturated fatty acid.

5. The plurality of core-shell structures according to claim 4, wherein the fatty acid is selected from a group consisting of myristoleic acid, palmitoleic acid, sapienic acid, oleic acid, elaidic acid, vaccenic acid, linoleic acid, linoelaidic acid, α-linolenic acid, arachidonic acid, eicosa-pentaenoic acid, erucic acid, docosahexaenoic acid, caprylic acid, capric acid, lauric acid, myristic acid, palmitic acid, stearic acid, arachidic acid, behenic acid, lignoceric acid and erotic acid.

6. The plurality of core-shell structures according to claim 1, wherein the diameter of 90% of the cores of the core-shell structures is in a range between 0.1 μm and 10 μm.

7. The plurality of core-shell structures according to claim 6, wherein the diameter of 90% of the cores is in a range between 0.15 μm and 0.75 μm.

8. A method for making the core-shell structure according to claim 1, comprising the steps of:

Providing a core of titanium oxide;
Treating the core with an ammonium salt selected from group consisting of ammonium carbamate and ammonium carbonate and with a metal salt, the metal salt being a salt of a metal selected from a group consisting of zinc, copper, vanadium, chromium, manganese, cobalt, molybdenum, tungsten, silver and mixtures thereof, to obtain an intermediate;
Calcining the intermediate to obtain the core-shell structure; and
Coating the core-shell structure obtained with a hydrophobic coating, on top of the shell, of at least one lipid, to obtain a coated core-shell structure.

9. The method according to claim 8, wherein a plurality of cores of titanium oxide is provided and the diameter of 90% of the cores is in a range between 0.1 μm and 10 μm.

10. The method according to claim 8, wherein the metal salt is a halide, and the halide is a chloride.

11. A non-therapeutic use of a plurality of core-shell structures according to claim 1 as a food additive, a feed additive or in a feedstuff.

12. The plurality of core-shell structures according to claim 1 for use as a medicament in the treatment of diarrhea or food poisoning.

13. A food additive, feed additive or feedstuff, comprising a plurality of core-shell structures, wherein the core-shell structure comprises a core of titanium oxide and a shell essentially comprising an oxide of a heavy metal selected from a group consisting of zinc, copper, vanadium, chromium, manganese, cobalt, molybdenum, tungsten, silver and mixtures thereof, wherein a concentration of the heavy metal is less than 100 ppm, wherein the core-shell structure has a specific surface of at least 20 m$^2$/g, wherein a diameter of 90% of the cores of the core-shell structures is in a range between 0.01 μm and 100 μm, and wherein the core-shell structure comprises a hydrophobic coating.

14. The food additive, feed additive or feedstuff according to claim 13, comprising the core-shell structures containing copper and zinc, wherein a ratio between copper and zinc is in a range of between 1:100 to 1:1.

* * * * *